(12) United States Patent
Park

(10) Patent No.: US 10,782,288 B2
(45) Date of Patent: Sep. 22, 2020

(54) MULTI-UNIT FOR CONDUCTING BIOCHEMICAL TEST AND IMMUNOLOGICAL TEST AND TESTING METHOD THEREOF

(71) Applicants: BIOBANK INC., Okcheon-gun, Chungcheongbuk-do (KR); Sung Sik Park, Daejeon (KR)

(72) Inventor: Sung Sik Park, Daejeon (KR)

(73) Assignee: BIOBANK INC., Chungcheongbuk-Do (KR)

( * ) Notice: Subject to any disclaimer, the term of this patent is extended or adjusted under 35 U.S.C. 154(b) by 366 days.

(21) Appl. No.: 15/553,302

(22) PCT Filed: May 12, 2017

(86) PCT No.: PCT/KR2017/004927
§ 371 (c)(1),
(2) Date: Aug. 24, 2017

(87) PCT Pub. No.: WO2018/052176
PCT Pub. Date: Mar. 22, 2018

(65) Prior Publication Data
US 2018/0246088 A1 Aug. 30, 2018

(30) Foreign Application Priority Data
Sep. 19, 2016 (KR) .......................... 10-2016-0118983

(51) Int. Cl.
*G01N 33/543* (2006.01)
(52) U.S. Cl.
CPC .............................. *G01N 33/54366* (2013.01)
(58) Field of Classification Search
CPC .............................................. G01N 33/54366
See application file for complete search history.

(56) References Cited

U.S. PATENT DOCUMENTS

| 6,083,682 A | * | 7/2000 | Campbell | ............ B01J 19/0046 422/130 |
| 6,485,690 B1 | * | 11/2002 | Pfost | .................... B01J 19/0046 422/552 |
| 2003/0202909 A1 | * | 10/2003 | Atkinson | ............ B01L 3/50255 422/400 |
| 2004/0149659 A1 | * | 8/2004 | Kane | .................... B01L 3/50255 210/649 |
| 2004/0208800 A1 | * | 10/2004 | Barth | .................... G01N 35/028 422/130 |
| 2005/0072030 A1 | * | 4/2005 | Wu | ............................ G09F 3/02 40/324 |
| 2005/0142033 A1 | * | 6/2005 | Glezer | .................. B01L 3/5085 422/400 |
| 2013/0143254 A1 | * | 6/2013 | Thomas | ............ G01N 33/54373 435/29 |
| 2016/0201037 A1 | * | 7/2016 | Tuan | ....................... C12M 23/12 435/373 |

FOREIGN PATENT DOCUMENTS

KR 10-0748181 B1 8/2007
KR 10-1608598 B1 4/2016

* cited by examiner

*Primary Examiner* — Ann Y Lam
(74) *Attorney, Agent, or Firm* — Bacon & Thomas, PLLC

(57) ABSTRACT

A multi-unit for performing a biochemical test and immunological response test and a test method using the same comprising an upper strip composed of a plurality of first strip wells including an indicator for the biochemical test; a lower strip composed of a plurality of second strip wells including DNA fragments or antibodies for the immunological response test; and plasma which reacts with the indicator, DNA fragments, or antibodies, and the strip enclosure composed of a plurality of third strip wells in which the upper strip and the lower strip are sequentially inserted and coupled. The bottom surface of the first strip well and the bottom surface of the second strip well are spaced apart from each other by a predetermined distance.

9 Claims, 3 Drawing Sheets

[FIG.1]
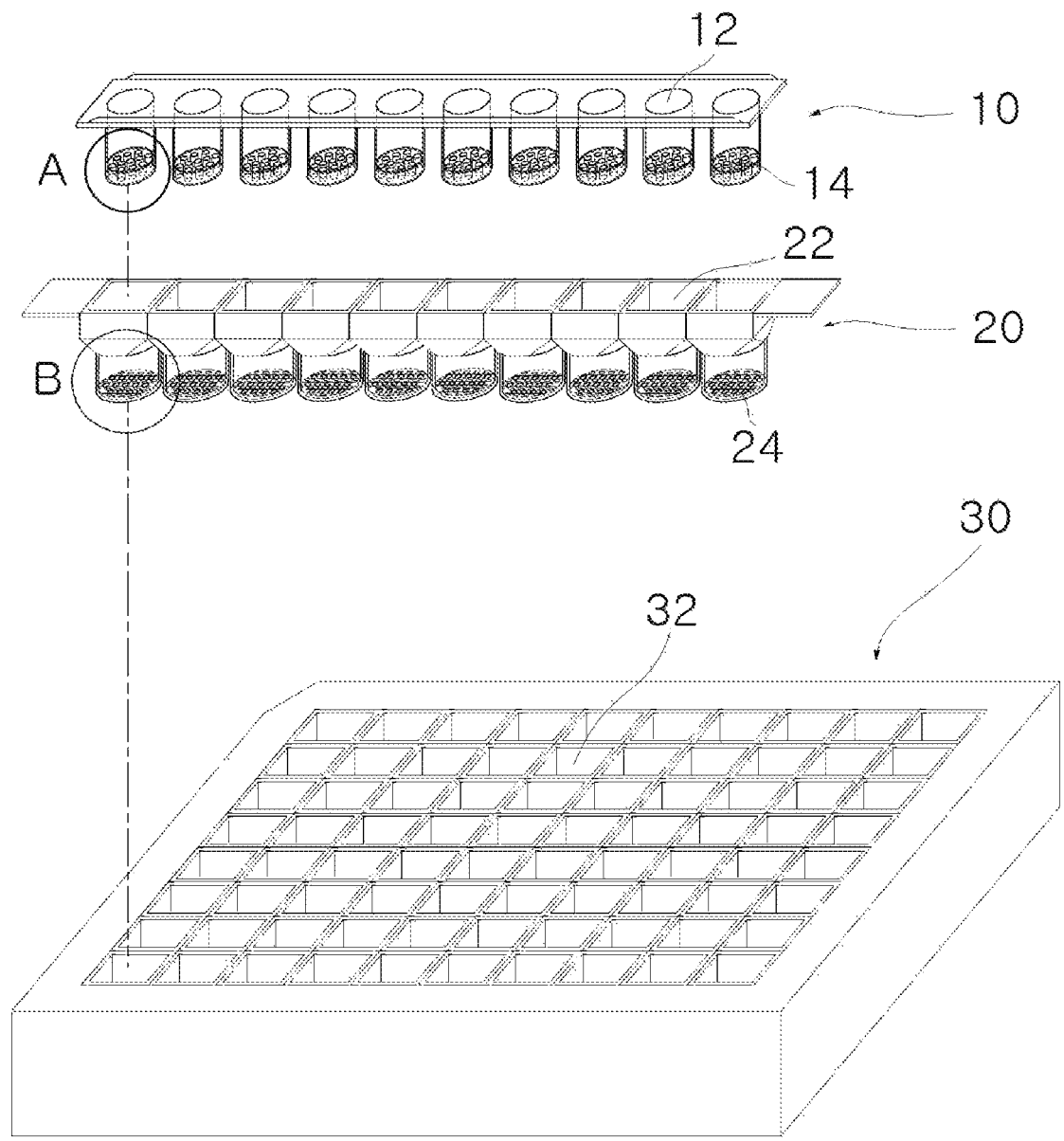

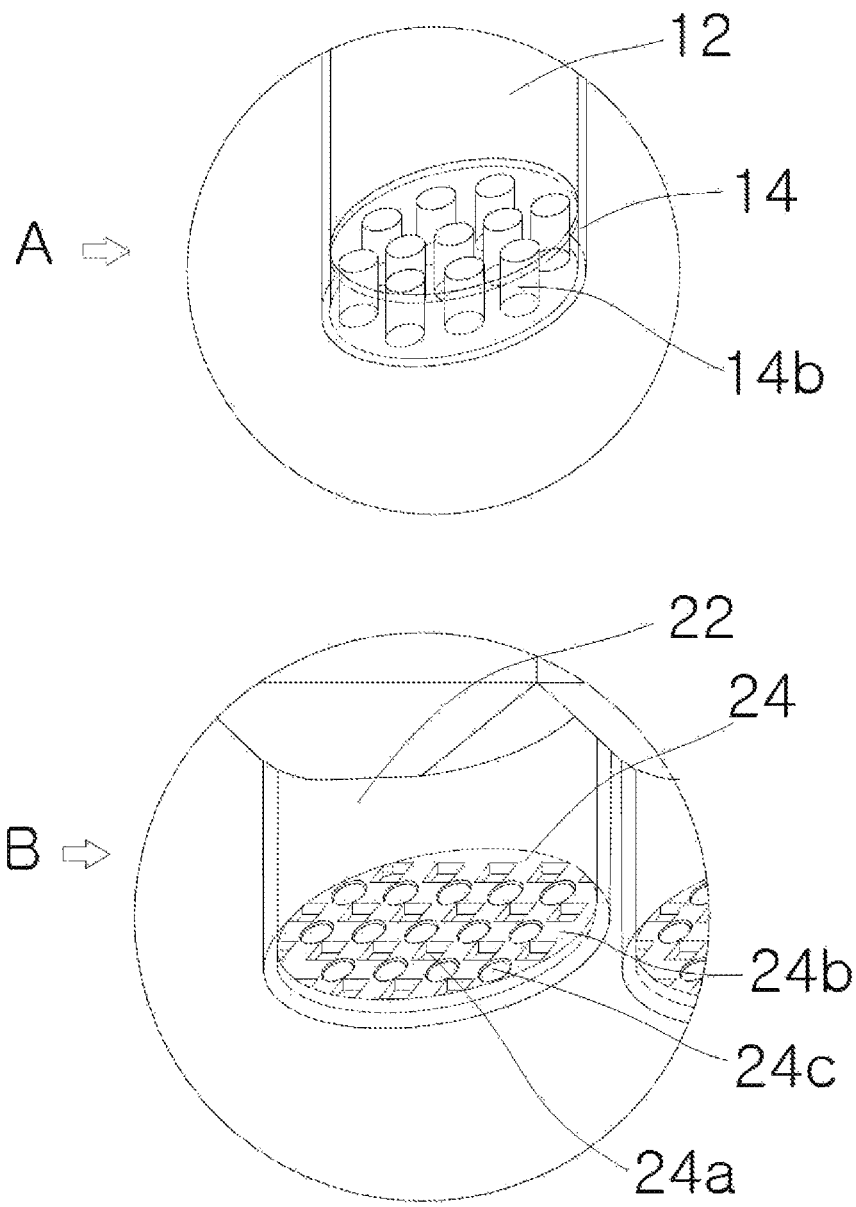
[FIG.2]

[FIG.3]
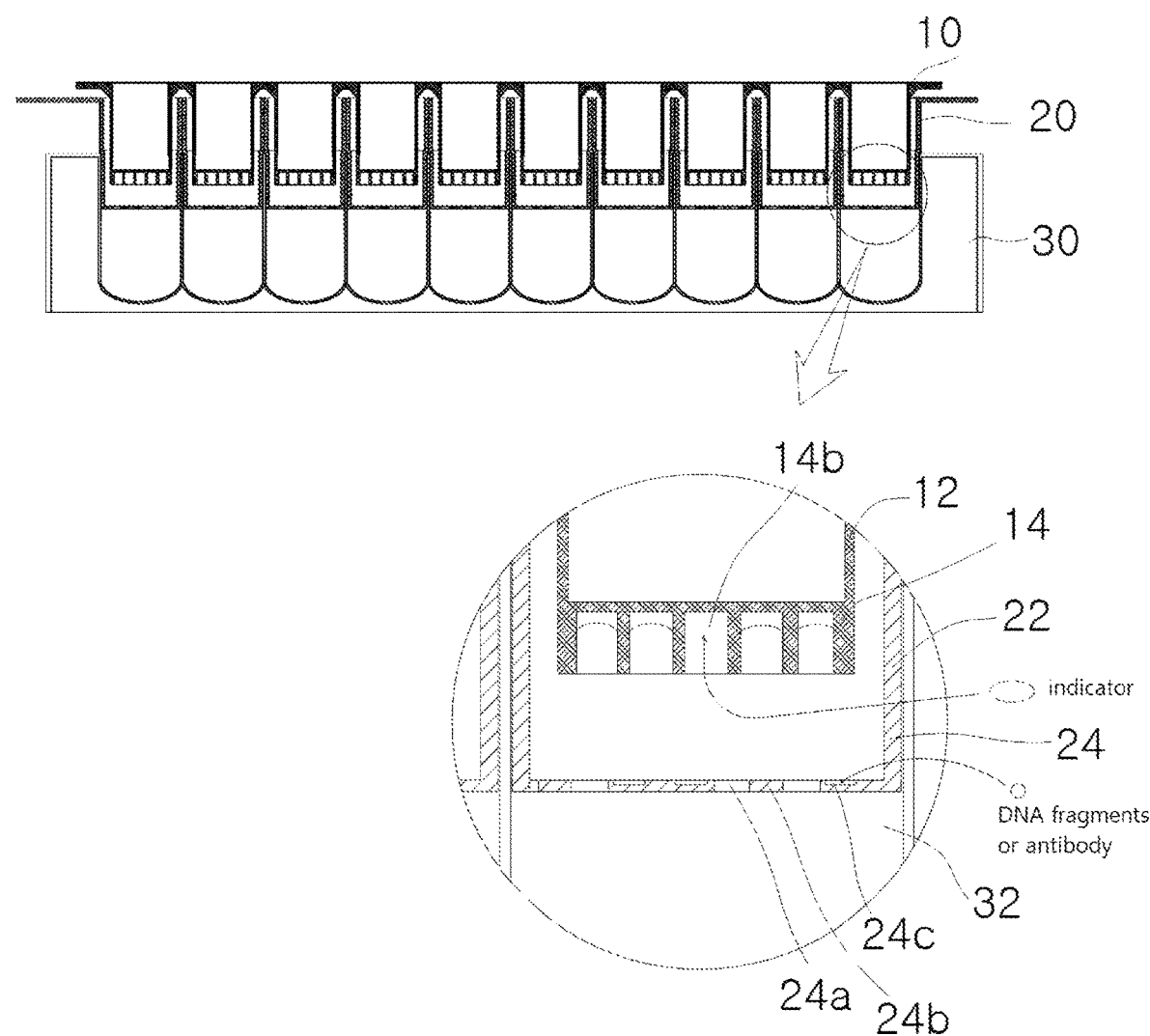

MULTI-UNIT FOR CONDUCTING BIOCHEMICAL TEST AND IMMUNOLOGICAL TEST AND TESTING METHOD THEREOF

BACKGROUND OF THE INVENTION

Field of the Invention

The present invention relates to a multi-unit for conducting a biochemical test and an immunological response test simultaneously and, more particularly, to a multi-unit which performs tests including biochemical test, immuno serological test, special chemical test, and genetic test with a single device simultaneously or individually, excluding the morphological test for counting the number of blood cells.

Background of the Related Art

Blood not only plays an important role in supplying oxygen, nutrients, hormones and nutritious substances to cells of all organs in the body, but also functions as a defense against infection and transports toxins and waste materials and thus, the changes that occur in the blood will change the blood components. Therefore, in order to accurately diagnose, treat and prognose diseases, various components of blood must be examined.

In order to test blood in this manner, special chemistry tests are carried out along with morphological, biochemical, and immunological serologic tests of the collected blood.

Here, the morphological examination of the blood uses hemocytes, hematocrit (hemocyte volume), red blood cells, white blood cells, platelet counts, blood cell counts to measure the cell percentage of white blood cells, and the blood smear test (the blood is applied on a slide with a thin layer, and the shape and number of the blood cells are observed with a microscope). The bleeding time, the coagulation time, and the capillary resistance are examined to diagnose and prognose the hemorrhagic tendency, blood disease, and infectious disease. At this time, the measurement is performed using an electrochemical method and a staining method.

In addition, in a biochemical method, an immunological method, and a special chemical method, blood cells in blood are firstly removed by centrifugation or the like, and the test is performed for an upper layer fluid (serum or plasma).

Generally, a biochemical method is a method in which serum (or plasma) is reacted with each indicator, and then the absorbance of a specific wavelength is measured and converted into a concentration. In accordance with the type of indicators used, the method is classified into a dry type and a wet type.

Wet type is the method mostly selected. Here, the indicator is in liquid form, causing it to react with plasma (serum). The dry type measures the absorbance by coating a thin film with the indicator for easy measurement and then reacting with the serum (plasma).

TABLE 1

| Biochemical Test Items | |
|---|---|
| Liver function related tests (SGOT, SGPT, ALP, r-GTP, Total protein, Albumin, Total bilirubin) | Acute/chronic hepatitis, liver disease, cirrhosis, alcoholic disorder, fatty liver, jaundice, nutritional status |
| Kidney function related tests (BUN, creatinine, uric acid) | Kidney failure, urticaria, gout disease |
| Lipid related tests (Total cholesterol, triglyceride) | Kidney failure, urticaria, gout disease Arteriosclerosis, fatty liver |

TABLE 1-continued

| Biochemical Test Items | |
|---|---|
| Heart related tests (LDH, CPK) | Myocardial infarction, multiple myositis |
| Pancreas and blood glucose related tests (Amylase, glucose) | Acute/chronic Pancreatitis, diabetes |

In addition, the immuno-serological test is an antigen and antibody test for various bacteria and viruses, and diagnoses B, C hepatitis, AIDS, syphilis and the like. In addition to diagnosis of rheumatic diseases, functions of immune cells are tested by isolating immune cells from blood. Further, by conducting specific immunoglobulin measurements in the blood for various other causes of allergies, the cause of allergy can be identified.

In most cases of immuno-serological test, a method of measuring the amount of the antibody (antigen) by labeling a marker to an antibody (antigen) to be examined by using an antigen-antibody immune response is generally adopted.

The method can be classified into Radioimmunoassay (RIA) for detecting signals using radioactive isotopes according to the type of the marker, enzyme-linked immunosorbent assay (ELISA) using signal amplification by enzyme, or EIA: Enzyme Immunoassay, Fluorescence Antibody (FA) detection using fluorescence, and Chemiluminescence Immunoassay using CLIA (Chemiluminescence Immunoassay). In addition, various classification is available according to the use of label substances or the type of substrates.

The special chemistry test is a test for the diagnosis of myocardial infarction, hyperthyroidism and hypothyroidism, various metabolites of congenital or acquired metabolic diseases, and this test includes a cancer marker test. Although the test may not directly diagnose cancer, but it can be used as an auxiliary means for diagnosis of cancer, and most of the tests are currently conducted in a form similar to immunoassay.

In recent years, a number of techniques for performing a large number of sample tests simultaneously with blood tests have been performed. Examples of such methods include DNA chips and lab-on-a-chip methods. These methods are mainly for conducting immuno serological test and genetic test simultaneously.

In the same fashion as the above, there is a desperate need to develop devices and kits for conducting tests including biochemical test, immuno serological test, special chemical test, and genetic test with a single device simultaneously or individually, in addition to the morphological test for counting the number of blood cells.

CITED REFERENCES (Cited reference 1) Korean Registered Patent No. 10-0748181
(Cited reference 2) Korean Registered Patent No. 10-1608598

SUMMARY OF THE INVENTION

Therefore, the present invention has been made to solve the above-mentioned problems. It is an object of the present invention to provide an automatic water quality analysis system which is capable of simultaneously testing biochemical tests and toxicity tests on water quality and a test method using the same.

In order to solve the above-mentioned problem, the multi-unit for performing the biochemical test and immunological response test is provided.

The multi-unit include:

an upper strip 10 composed of a plurality of first strip wells 12;

a lower strip 20 composed of a plurality of second strip wells 22; and a strip enclosure 30 composed of a plurality of third strip wells 32 in which the upper strip 10 and the lower strip (20) are sequentially inserted and coupled, wherein a lower surface of a bottom of the upper strip (10) is coupled to an upper surface of a bottom of the lower strip (20) with a space therebetween.

In addition, in the multi-unit for conducting the biochemical test and the immunological response test, it is included:

a closed bottom surface 14 of each of the first strip well (12) of the upper strip 10 includes a plurality of reagent spaces (14b) which are opened downward.

In addition, in the multi-unit for conducting the biochemical test and the immunological response test according to the present invention it is included:

a bottom surface 24 of each of the second strip well 22 of the lower strip 20 is in a mesh structure composed of a plurality of through holes and line portions.

In addition, in the multi-unit for conducting the biochemical test and the immunological response test according to the present invention, it is included:

a predetermined size of a groove is formed on the mesh structure and each of the line portions.

In addition, in the multi-unit for conducting the biochemical test and the immunological response test according to the present invention, an indicator for conducting biochemical test is provided in the upper strip 10, a DNA fragment or antibody for immunological test is provided in the lower strip 20, the indicator or plasma which reacts with the DNA fragment or antibody is provided in the strip case 30.

In addition, in the multi-unit for conducting the biochemical test and the immunological response test according to the present invention, it is included:

the indicator for conducting biochemical test is dispensed into each of a plurality of reagent spaces 14b provided in the upper strip 10, followed by drying and fixing, the DNA fragments or antibody for conducting the immunological test are provided in the line portion of the mesh structure or the groove provided in the lower strip 20 by being spotted.

In addition, in the multi-unit for conducting the biochemical test and the immunological response test according to the present invention, it is included:

multi-unit is capable of conducting the biochemical test and immunological test separately or simultaneously.

A testing method using a multi-unit for conducting a biochemical test and an immunological test, including:

preparing a multi-unit for conducting a biochemical test and an immunological test, the multi-unit including an upper strip 10 composed of a plurality of first strip wells 12 wherein a closed bottom surface 14 of each of the first strip well 12 of the upper strip 10 includes a plurality of reagent spaces 14b which are opened downward; a lower strip 20 composed of a plurality of second strip wells 22 wherein a bottom surface 24 of each of the second strip well 22 of the lower strip 20 is in a mesh structure composed of a plurality of through holes and line portions; and a strip case 30 composed of a plurality of third strip wells 32 in which plasma is contained;

dispensing an indicator into a plurality of reagent spaces 14b of the upper strip 10, drying, and fixing the same;

coupling the upper strip 10 with the strip enclosure 30 containing plasma at reacting at temperature of 30-40° C. for 5-20 minutes; and moving the upper strip 10 of which reaction is completed to an absorbance measuring unit to measure absorbance and converting concentration.

The testing method using a multi-unit for conducting a biochemical test and an immunological test includes:

spotting and fixing DNA fragments or antibody on an upper surface of a plurality of line portions or groove 24C on the line portion of the lower strip 20; coupling the lower strip (20) with the strip enclosure 30 containing plasma and reacting with the plasma; and moving the lower strip 20 of which reaction is completed to an absorbance measuring unit and measuring by a spectrophotometer.

Using the multi-unit for conducting the biochemical test and the immuno serological test according to the present invention and the test method thereof, there is the effect of enabling tests including biochemical test, immuno serological test, special chemical test, and genetic test with a single device simultaneously or individually, except the morphological test for counting the number of blood cells.

BRIEF DESCRIPTION OF THE DRAWINGS

Further objects and advantages of the invention can be more fully understood from the following detailed description taken in conjunction with the accompanying drawings in which:

FIG. 1 is an exploded perspective view schematically showing an overall structure and an internal structure of a multi-unit that performs a biochemical test and an immunological reaction test according to an embodiment of the present invention, FIG. 2 is an enlarged perspective view of portions A and B of FIG. 1, FIG. 3 is an enlarged view of the state of FIG. 1 and the state in which the inspection reagent or the like is disposed.

DETAILED DESCRIPTION OF THE PREFERRED EMBODIMENT

The preferred embodiments of the invention will be hereinafter described in more detail with reference to the accompanying drawings.

Embodiments of the present invention will be described in more detail hereinafter with reference to the accompanying drawings. The present invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the shapes and sizes of respective elements may be exaggerated for clarity.

Hereinafter, preferred embodiments of a multi-unit for conducting a biochemical test and an immunological reaction test according to the present invention will be described in detail with reference to the accompanying drawings.

FIG. 1 is an exploded perspective view schematically showing an overall structure and an internal structure of a multi-unit that performs a biochemical test and an immunological reaction test according to an embodiment of the present invention; FIG. 2 is an enlarged perspective view of portions A and B of FIG. 1; FIG. 3 is an enlarged view of the state of FIG. 1 and the state in which the inspection reagent or the like is disposed.

As illustrated in FIGS. 1 to 3, a multi-unit 1 for simultaneously performing a biochemical test and an immunological reaction test according to the present invention includes an upper strip 10 composed of a plurality of first strip wells 12; a lower strip 20 composed of a plurality of second strip wells 22; and a plurality of third strip wells 32 in which the upper strip and the lower strip are sequentially coupled to each other in an upward direction.

The upper strip 10 is composed of a plurality of first strip wells 12 and has a closed bottom surface 14 of each first strip well 12 forming the upper strip 10, and a plurality of reagent spaces 14b opened in a downward direction at the closed bottom surface 14 of the first strip well 12.

The upper strip 10 is for performing a biochemical test. The dry reagent is dispensed into each of the plurality of reagent spaces 14b, and then dried and fixed.

The lower strip 20 is composed of a plurality of second strip wells 22 and the bottom surface 24 of each second strip well 22 forming the lower strip 20 is in a mesh structure having a lattice pattern composed of a plurality of through holes 24a and the line portions 24b. Each of the line portions has a predetermined width. In addition, a groove 24c having a predetermined size may be formed in each line portion.

The lower strip 20 is for performing an immunological test, and DNA fragments or antibodies (or antigens) are spotted and fixed in the grooves formed in a plurality of line portions or line portions of the mesh structure, respectively.

The upper surface of the bottom of the mesh structure of the aforementioned lower strip is positioned at a predetermined distance from the bottom surface of the upper strip so that each test can be carried out simultaneously or individually in the upper strip and the lower strip.

The strip enclosure 30 is provided with a plurality of third strip wells 32 having an appropriate depth. In each of the third strip wells 32, an upper layer solution (blood serum or blood plasma) from which blood cells in the blood are removed is contained at a predetermined depth, and the first strip well of the upper strip and the second strip well of the lower strip are sequentially coupled in the upward direction.

Hereinafter, a method of performing the test using the multi-unit 1 that simultaneously performs the biochemical test and the immunological response test according to the present invention will be described as follows.

The multi-unit for conducting a biochemical test and an immunological reaction test is prepared. The multi-unit includes an upper strip 10 composed of a plurality of first strip wells 12 wherein a closed bottom surface 14 of each of the first strip well 12 of the upper strip 10 includes a plurality of reagent spaces 14b which are opened downward; a lower strip 20 composed of a plurality of second strip wells 22 wherein a bottom surface 24 of each of the second strip well 22 of the lower strip 20 is in a mesh structure composed of a plurality of through holes and line portions; and a strip enclosure 30 composed of a plurality of third strip wells 32 in which plasma is contained.

Next, for the biochemical test, a dry indicator corresponding to a test item to be measured is dispensed into each of a plurality of reagent spaces 14b of a plurality of first strip wells 12 of the upper strip 10, followed by drying and fixing.

Next, the upper strip 10 is inserted and coupled into the strip enclosure 30 carrying the plasma and reacted at a temperature of 30 to 40° C., preferably 37° C., for 5 to 20 minutes, preferably 10 minutes.

After completion of the reaction, the upper strip 10 is moved to the absorbance measurement unit, and the absorbance is measured and converted into a concentration to perform a biochemical test.

Further, for the purpose of immunity test, in the upper surface or the groove 24c of each of the line portions 24b in a mesh structure of the bottom surface 24 of the plurality of second strip wells 22 of the lower strip 20, each of the DNA fragments or antibodies (antigens) is spotted and fixed.

Next, the lower strip 20 is inserted and coupled to the strip enclosure 30 carrying the plasma so that the upper surface of each line portion 24b of the mesh structure of the second strip well 22 of the lower strip, the DNA fragment or the antibody (antigen) contained in the groove 24c is reacted with the plasma.

After the reaction of the lower strip 20 is completed, the absorbance is measured using a spectrophotometer to perform an immunological response test.

The immunological reaction test is generally performed by using an antigen-antibody immune response. Generally, an antibody (antigen) to be tested is labeled with a marker, and the amount of the antibody is measured. Here, a spectrophotometer is used according to labeled substances.

At this time, a fluorescent reader is used when the labeled substance is fluorescent, and a CLIA reader is used when the labeled substance is CLIA. Here, in order to carry out the genetic testing, a separate hybridization process of detecting a labeled DNA or RNA fragment, which is arranged in a complementary manner to detect DNA or RNA having a specific sequence, should be conducted ahead of the measurement.

Here, the biochemical test and the immunological response test can be performed individually or simultaneously. At this time, the first strip wells 12 of the upper strip and the second strip wells 22 of the lower strip are inserted and coupled to the strip enclosure 30 so as to sequentially correspond to the third strip well 32. The bottom surface of the first strip well and the bottom surface of the second strip well are spaced apart from each other by a predetermined distance.

This allows the plasma passing through the through holes of the mesh structure of the second strip well 22 to react with each reagent contained in the plurality of reagent spaces 14b of the first strip well 12. At the same time, the DNA fragment or antibody (antigen) provided on the upper surface or groove 24c of each line portion 24b of the mesh structure of the second strip well 22 is reacted with the plasma and is not affected by the first strip well.

While the present invention have been described in connection with the exemplary embodiments illustrated in the drawings, it will be appreciated that they are merely an illustrative embodiments and various equivalent modifications and variations of the embodiments can be made by a person having an ordinary skill in the art without departing from the spirit and scope of the present invention. Therefore, the appended claims also include such modifications and variations falling within the true technical scope of the present invention.

What is claimed is:
1. A multi-unit for conducting a biochemical test and an immunological response test, the multi-unit comprising:
an upper strip composed of a plurality of first strip wells;
a lower strip composed of a plurality of second strip wells; and a strip enclosure composed of a plurality of third strip wells in which the upper strip and the lower strip are sequentially inserted and coupled, wherein a lower surface of a bottom of the upper strip is coupled to an upper surface of a bottom of the lower strip with a space therebetween.

2. The multi-unit according to claim 1, wherein a closed bottom surface of each of the first strip well of the upper strip includes a plurality of reagent spaces which are opened downward.

3. The multi-unit according to claim 1, a bottom surface of each of the second strip well of the lower strip is in a mesh structure composed of a plurality of through holes and line portions.

4. The multi-unit according to claim 3, wherein a predetermined size of a groove is formed on the mesh structure and each of the line portions.

5. The multi-unit according to claim 1, wherein an indicator for conducting biochemical test is provided in the upper strip, and a DNA fragment or antibody for immunological test is provided in the lower strip, wherein the indicator or plasma which reacts with the DNA fragment or antibody is provided in the strip case.

6. The multi-unit according to claim 5, wherein the indicator for conducting biochemical test is dispensed into each of a plurality of reagent spaces provided in the upper strip, followed by drying and fixing, and wherein the DNA fragments or antibody for conducting the immunological test are provided in a line portion of a mesh structure or a groove provided in the lower strip by being spotted.

7. The multi-unit according to claim 1, wherein the multi-unit is capable of conducting the biochemical test and immunological test separately or simultaneously.

8. A testing method using a multi-unit for conducting a biochemical test and an immunological test, the method comprising:

preparing a multi-unit for conducting a biochemical test and an immunological test, the multi-unit including an upper strip composed of a plurality of first strip wells wherein a closed bottom surface of each of the first strip well of the upper strip includes a plurality of reagent spaces which are opened downward; a lower strip composed of a plurality of second strip wells wherein a bottom surface of each of the second strip well of the lower strip is in a mesh structure composed of a plurality of through holes and line portions; and a strip enclosure composed of a plurality of third strip wells in which plasma is contained;

dispensing an indicator into a plurality of reagent spaces of the upper strip, drying, and fixing the same;

coupling the upper strip with the strip enclosure containing plasma and reacting at temperature of 30-40° C. for 5-20 minutes; and moving the upper strip after reaction of the upper strip is completed to an absorbance measuring unit to measure absorbance and converting concentration.

9. The testing method according to claim 8, wherein the multi-unit further conducts an immunological test comprising:

spotting and fixing DNA fragments or antibody on an upper surface of a plurality of line portions or groove on the line portion of the lower strip;

coupling the lower strip with the strip enclosure containing plasma and reacting with the plasma; and moving the lower strip after reaction of the lower strip is completed to an absorbance measuring unit and measuring by a spectrophotometer.

\* \* \* \* \*